United States Patent
Greuel

(10) Patent No.: US 9,045,358 B2
(45) Date of Patent: Jun. 2, 2015

(54) UV DISINFECTING DEVICE

(75) Inventor: Georg Greuel, Roetgen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 788 days.

(21) Appl. No.: 13/256,520

(22) PCT Filed: Mar. 19, 2010

(86) PCT No.: PCT/IB2010/051196
§ 371 (c)(1),
(2), (4) Date: Sep. 14, 2011

(87) PCT Pub. No.: WO2010/109389
PCT Pub. Date: Sep. 30, 2010

(65) Prior Publication Data
US 2012/0006995 A1  Jan. 12, 2012

(30) Foreign Application Priority Data

Mar. 26, 2009 (EP) .................................... 09156330

(51) Int. Cl.
*G21K 5/00* (2006.01)
*C02F 1/32* (2006.01)

(52) U.S. Cl.
CPC ..................................... *C02F 1/325* (2013.01)

(58) Field of Classification Search
CPC ........... A61L 2/10; A61L 9/20; A61L 2/0047; A61L 2202/122; H01J 63/02; B01J 19/123
USPC ............... 250/453.11–455.11, 504 R; 422/24
See application file for complete search history.

(56) References Cited

U.S. PATENT DOCUMENTS

| | | | |
|---|---|---|---|
| 3,843,521 A * | 10/1974 | Zeff ................................. 10/138 |
| 5,581,152 A * | 12/1996 | Matsuno et al. ............... 313/634 |
| 6,084,360 A * | 7/2000 | Yokokawa et al. ........... 315/287 |
| 6,398,970 B1 | 6/2002 | Justel et al. |
| 6,773,608 B1 | 8/2004 | Hallett et al. |
| 6,953,523 B2 | 10/2005 | Vandenbelt et al. |
| 8,035,289 B2 | 10/2011 | Auday |
| 2003/0086818 A1* | 5/2003 | Holley et al. .................... 422/24 |
| 2005/0258108 A1* | 11/2005 | Sanford ........................ 210/748 |
| 2008/0061667 A1* | 3/2008 | Gaertner et al. ............... 313/113 |
| 2009/0218512 A1* | 9/2009 | Ranta et al. ............... 250/455.11 |
| 2009/0250626 A1* | 10/2009 | Schlesser et al. ......... 250/455.11 |
| 2010/0032589 A1* | 2/2010 | Leben ....................... 250/504 R |

(Continued)

FOREIGN PATENT DOCUMENTS

CN   2155876 Y   2/1994
WO   2006116828 A1   11/2006

(Continued)

*Primary Examiner* — Michael Maskell

(57) ABSTRACT

A disinfecting device is proposed that is well suited for household and outdoor use. The device comprises a container housing 12 with an interior volume 24, which may contain an object or a liquid to be disinfected. The container housing 12 comprises a side wall 16 and an end cover 14. A dielectric barrier discharge lamp 32 is provided for emitting ultraviolet light into the volume 24. The lamp 32 comprises a lamp vessel 34 with gas filling and electrodes 42, 44 arranged electrically insulated from the gas filling. An alternating voltage applied to the electrodes 42, 44 causes a discharge in the gas filling. The lamp vessel 34 has a planar window from which during the discharge ultraviolet light 46 is emitted. The window is arranged in the end cover 14.

13 Claims, 4 Drawing Sheets

(56) References Cited

U.S. PATENT DOCUMENTS

2010/0044319 A1* 2/2010 Engel et al. ............... 210/746
2011/0079732 A1* 4/2011 Kreitenberg ............ 250/455.11
2011/0315893 A1* 12/2011 Pugh et al. .............. 250/455.11

FOREIGN PATENT DOCUMENTS

| WO | 2007078294 A1 | 7/2007 |
| WO | 2007086829 A1 | 8/2007 |

* cited by examiner

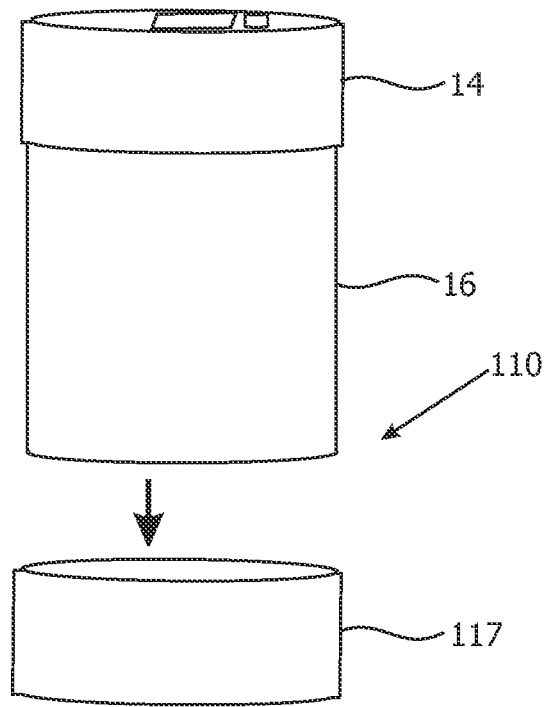
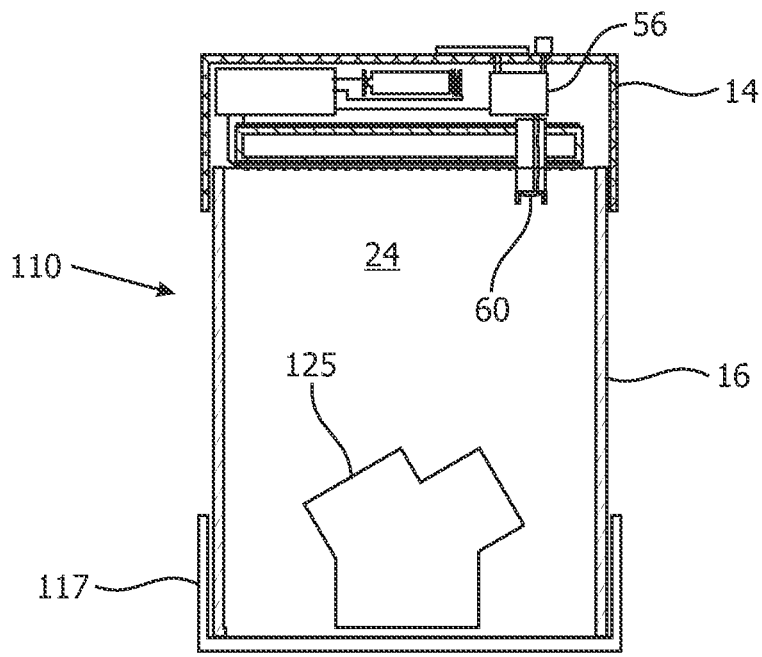

UV DISINFECTING DEVICE

FIELD OF THE INVENTION

The invention relates to the field of disinfecting devices, and more specifically to a device for disinfecting objects and/or liquids by ultraviolet (UV) light.

BACKGROUND OF THE INVENTION

Ultraviolet light may be used for disinfection of liquids or objects. For example, it is known to use UV radiation generated by low-pressure or medium-pressure mercury arc discharge lamps for treatment of waste water. UV-C radiation (with a wavelength of 200-280 nm) achieves disinfection by damaging the DNA of contaminating micro-organisms. However, up to now UV disinfection has not found widespread use in household applications.

US-A-2005/0258108 describes a container for purifying water. The container has a lid with one or more UV LEDs as radiation source. Also, integrated in the lid is a solar panel and a rechargeable power source to operate the LEDs. The lid is removably attached to the container by way of threads or a snap-fit connection. In alternate embodiments, the UV LEDs are arranged on an elongate member extending from the lid into the container or on ribs arranged on the container wall. The LEDs emit light in the UV-C range of 200 to 265 nm. The device includes an indicator showing sufficient disinfection, which may be controlled based on the irradiation time alone, or may process the input from a motion sensor to account for the fact that agitated contents will be purified more rapidly.

SUMMARY OF THE INVENTION

It is an object of the invention to provide a disinfecting device well suited for household and outdoor use.

This object is achieved according to the invention by the device defined in the claims. Dependent claims refer to preferred embodiments of the invention.

According to the invention, the device comprises a container housing with an interior volume. The interior volume is defined by the interior extensions of at least a side wall and an end cover, which may e.g. be a top cover. It should be noted, here and in the following description, that references such as "top", "bottom" and "side", referring to an upright position of the device, are used to illustrate the positions of the parts relative to each other, and should not be construed as limiting with regard to possible orientations of the device itself.

According to the invention, a UV lamp is arranged such that UV light is emitted from a window in the end cover, e.g. in the top cover of the container housing. The lamp proposed according to the invention is a dielectric barrier discharge lamp especially adapted for fitting in the end cover.

The lamp comprises a lamp vessel with a gas filling and electrodes arranged electrically insulated from the gas filling. The dielectric arranged between the electrodes and the gas filling will typically be the material of the lamp vessel, preferably Quartz. For the gas filling, different compositions may be used. The lamp is driven by an alternating voltage which causes a dielectric barrier discharge to generate light. The spectral composition of the light depends on the gas filling. As will be explained with regard to the preferred embodiment, the gas filling preferably comprises Xenon. Dielectric barrier Xenon excimer discharge lamps have an emission band centered at 172 nm. Alternatively, the gas filling may comprise one or more of Xenon, Krypton, Argon, Neon and halides. For gas fillings which generate light outside the UVC range of 200 to 280 nm, a phosphor conversion layer may be deposited on the inside of the lamp vessel. The preferred embodiment comprises a gas filling consisting of Xenon as main constituent, and a phosphor layer as described e.g. in U.S. Pat. No. 6,398,970 B1.

The lamp vessel of the dielectric barrier discharge lamp has a planar window from which light from the discharge is emitted. Preferably, the shape of the lamp is entirely planar, where electrodes are arranged on opposing planar sides of a flat discharge vessel.

The dielectric barrier discharge lamp with its window is arranged in the end cover, such that the interior volume of the container housing is illuminated by the light emitted from the lamp. In a preferred embodiment, the side of the lamp directed towards the interior of the container is covered with a partly transparent electrode, e.g. a wire mesh or a printed mesh like electrode structure, and connected to the ground electrode of a high voltage transformer. The electrode allows passage of the UV light emitted by the lamp and provides ground electrical contact to the outer side of the excimer lamp.

According to the invention, there is thus proposed a disinfecting device with an interior volume that is illuminated by UV light from a specially adapted dielectric barrier discharge lamp arranged within the end cover. The lamp is well suited for efficient production of UV light. Further, its geometry with a planar window is well integrated in the container housing. Thus, a very compact device is provided which may efficiently treat objects and/or fluids arranged within the volume.

According to a preferred embodiment of the invention, the interior volume of the container has cylindrical shape. In the present context this is understood to mean that the cross-section of the interior volume, at least in a central portion over 50% or more of its length, remains the same. Here, the cross-sectional shape may be e.g. circular, square, rectangular or other. For a cylindrical shape, illumination of the volume from the direction of the end cover is effective to treat all parts of the volume. Further, a corresponding simple shape of the side wall may be produced at low cost.

Further, it is preferred that the device is portable, meaning that its size and weight allow easy handling and transportation. Preferably, the container housing may have a shape and size suitable to be used as a drinking cup. While in principal it is possible to provide a device which may be powered by connection to the mains voltage, it is preferred to have a battery-powered device. According to a preferred embodiment of the invention, the device comprises a battery, which may be rechargeable, and a ballast device for the lamp. The ballast device is electrically supplied from the battery and generates an appropriate driving voltage for the lamp, i.e. an alternating voltage of amplitude, wave form and frequency chosen to obtain a suitable discharge within the lamp vessel.

According to one embodiment of the invention, the device has a removable end (in this case preferably: top) cover and is shaped such that the interior volume may be filled with a liquid. Thus, the device may be used for treating liquids such as drinking water.

In a further embodiment, the container housing comprises besides the end cover also a cover on the opposite end. In this case, where it is preferred that the end cover is fixed to the side wall, the opposite end cover is removable to open the container. While this type of device may eventually also be used for treating liquids, where the liquid is illuminated by UV light from the end cover below, it is primarily intended to be used for the treatment of objects, which may be placed within the interior volume by putting the container housing over them.

According to a further embodiment, both end covers of the container housing may each comprise a dielectric barrier discharge lamp for illuminating the interior of the container. Thus, the interior of the container may be very intensely illuminated by UV radiation to obtain thorough disinfection. In fact, the end covers may be constructed substantially identical, i.e. both with lamp, driver electronics and an energy source, e.g. a battery. Preferably, they are electrically connected to synchronize operation.

UV radiation, and especially the here preferred UV-C radiation of 200-280 mm is dangerous to the human skin and may cause severe eye damage. Therefore, for safety reasons it is preferred that the device comprises a closure sensor to detect an opening of the volume. Control means of the device cooperate with the closure sensor to operate the lamp only if no opening is detected. The closure sensor may be a mechanical sensor detecting if a removable end cover and/or opposite end cover is closed. Alternatively, other types of sensors may be used, for example an optical sensor sensing an ambient light level, where the control means only operate the lamp if prior to operation no light is detected within the volume.

According to a further preferred embodiment, a closure sensor for optically sensing closure of the container may comprise a light source, preferably in the visible range, and a photo sensor detecting light in this range, where the light source and the photo sensor are arranged without direct optical contact. The photo sensor will then only be illuminated by the light source if the container is correctly closed, i.e. if a detachable end cover is firmly seated on the container, such that the light emitted from the light source is reflected into the photo sensor.

The different types of closure sensors described above may be combined to increase safety.

In order to monitor operation or to ensure effective treatment the device may comprise a UV sensor. Since operation of the lamp within the closed volume may not otherwise be observed from the outside, the UV sensor may simply detect the presence of UV light during the treatment to signal correct operation. Alternatively, the UV sensor may sense a level of UV intensity within the volume. According to a preferred embodiment, there is a control unit provided which processes the signal from the sensor to determine a UV dose value, e.g. corresponding to an intensity value integrated over time. The UV dose value is indicative of the treatment of objects or liquids contained within the volume. Since the UV light output of the lamp may vary over the lifetime, determination of a UV dose value is superior to simply regarding the treatment time.

In the case of a liquid with limited transmittance, i.e. with suspended particles, it may be advisable to determine an amount of transmitted UV light. Accordingly, in a preferred embodiment the sensor is arranged within the end cover, and the container housing comprises a reflective surface at the opposite end. The sensor then observes the intensity of ultraviolet light emitted from the lamp, e.g. through a liquid contained within the volume, and reflected at the reflective surface. Here, the sensor preferably does not receive light emitted from the lamp directly, but only via the reflection. Reflective surfaces to be used comprise e.g. Aluminum, stainless steel, PTFE (Teflon), Al2O3 ceramic. It is not required that the container surface at the opposite end as a whole is made from these materials; instead, a sheet like piece can be attached to the inner side of the container, to reflect the UV light from the opposite emitting cover towards the detector opening.

As a further embodiment, a photo sensor sensitive to UV light may be arranged at the end of the container opposite to the lamp. Thus, operation of a lamp may be monitored directly, attenuated during the passage through the container. In the case of lamps arranged at both ends of the container, each end may also comprise a sensor for monitoring operation of the lamp on the opposite side.

The lamp may, in order to be effective for disinfection, emit UV light of different spectral composition. On one hand, the emitted spectrum depends on the gas filling of the dielectric barrier discharge lamp. According to a preferred embodiment, there may further be arranged a luminescent layer on the lamp vessel, e.g. on the entire surface of the window or on parts thereof. If the luminescent layer is stimulated by (primary) light emitted from the discharge, it emits (secondary) ultraviolet light of a different wavelength. As will become apparent in connection with description of the preferred embodiments, the composition of the luminescent layer may be specially chosen to obtain a desired spectral composition for effective disinfection.

BRIEF DESCRIPTION OF THE DRAWINGS

The above and other objects, features and advantages of the present invention will become apparent from and elucidated with reference to the embodiments described hereinafter.

In the figures,

FIG. 5 shows a perspective side view of a second embodiment of a disinfecting device;

FIG. 6 shows a partly symbolical cross-sectional view of the device of FIG. 4;

DETAILED DESCRIPTION OF EMBODIMENTS

Figure 1:
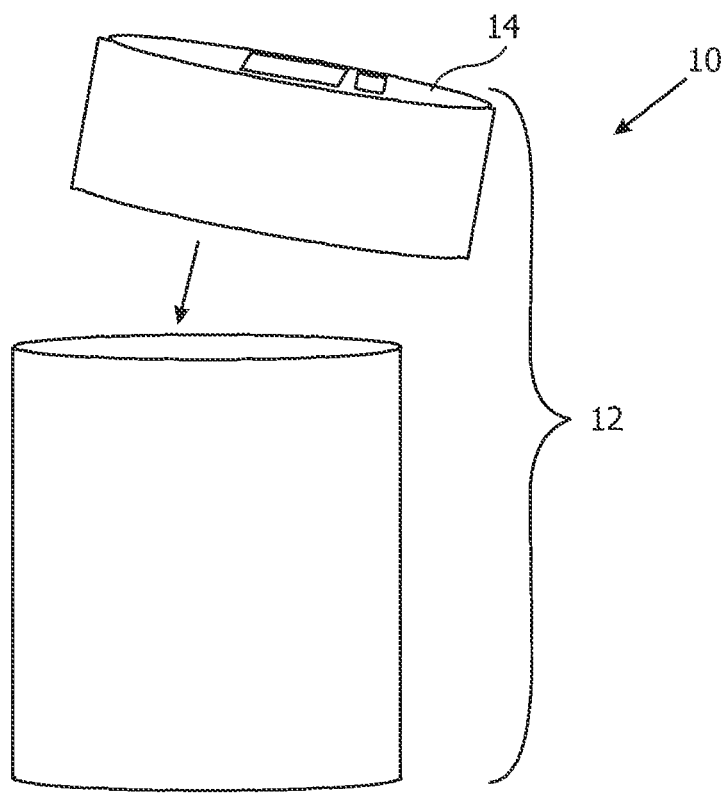
FIG. 1 shows a perspective side view of a first, preferred embodiment of a disinfecting device.

FIG. 1 shows a first embodiment of a disinfection device 10 consisting of a container housing 12 with a detachable top cover 14.

Figure 2:
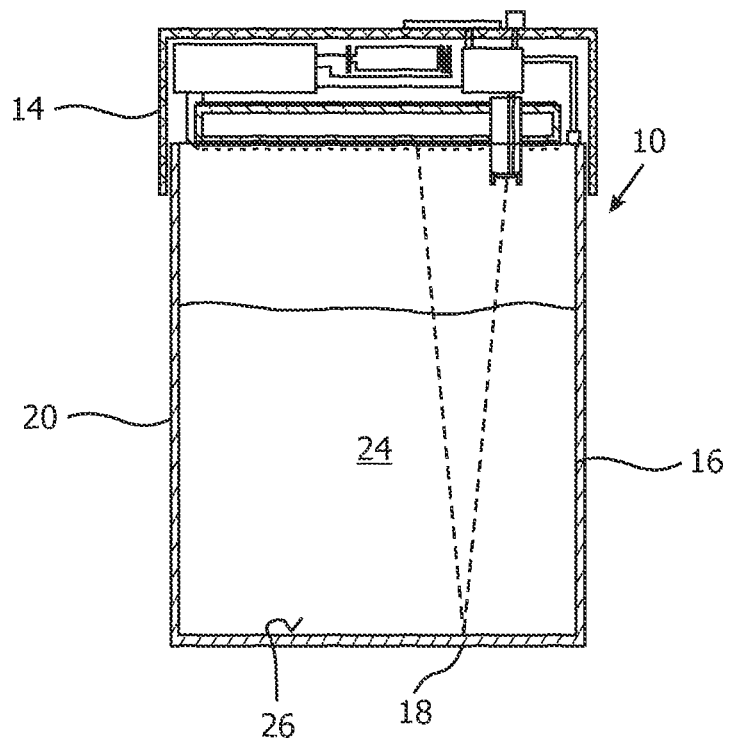
FIG. 2 shows a partly symbolical cross-sectional view of the device of FIG. 1.

FIG. 2 shows the device 10 in cross-section. The container housing 12 consists of a side wall 16, a bottom 18 and the detachable lid 14 acting as top cover. As shown in FIG. 2, the side wall 16 and bottom 18 are formed in one piece as a stainless steel container 20. The shape of the side wall 16 is such that it is cylindrical with a constant, circular cross-section over the entire height. Due to its construction as one piece, the container housing 12 is sealed to the side and bottom, such that it may contain a liquid in its interior cavity 24. The side wall 16 and the bottom 18 together form a cup, which may e.g. contain water, and which has a shape and size such that it may be handled as a drinking cup, i.e. used to directly drink from the cup.

Figure 3:
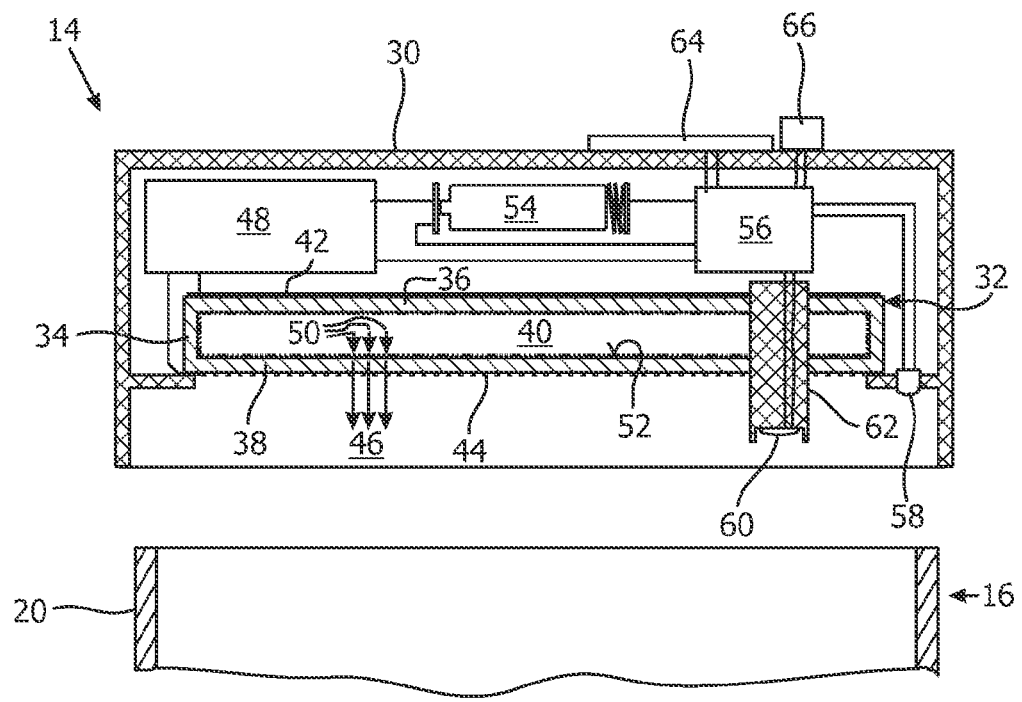
FIG. 3 shows an enlarged partly symbolical cross-sectional view of the top cover of the device according to FIG. 1, FIG. 2.

FIG. 3 shows in an enlarged sectional view of the lid 14 (upper end cover) of the device 10. In a plastic housing 30 the lower part of which fits on the side wall 16, a dielectric barrier discharge lamp 32 is arranged together with driver and control circuitry.

The dielectric barrier discharge lamp 32 consists of a disc-shaped, closed glass vessel where a planar upper wall 36 and an equally planar lower wall 38 of the glass vessel 34 are arranged in parallel at a distance defining a closed discharge space 40.

Over the outer area of the upper wall 36, a first electrode 42 is provided, e.g. as a metal coating on this part of the glass vessel 34. A second electrode 44 is provided on the outer side of the lower wall 38 in a way to allow capacitive coupling to the discharge space 40 while still allowing light 46 to be emitted into the interior volume of the container housing 12. For example, the second electrode 44 may be provided as a wire grid. As a further alternative, a printed conductive mesh-like structure may be used for the electrode 44.

The gas filling within the discharge space 40 consists of Xenon at a pressure of 50-500 mbar. To operate the lamp 32, a driver circuit 48 is provided to supply a pulse shaped driving voltage at the lamp electrodes 42, 44. Hereby, a dielectric barrier discharge is excited within discharge space 40, such that primary light 50 of VUV wavelength of 172 nm is generated. The amplitude of the voltage is between 2 kV and 4 kV peak, and the peak to peak voltage is between 2.5 kV and 6 kV. The pulse repetition frequency is between 30 kHz and 150 kHz, and the duty cycle between 5% and 50%. The lamp input power is between 1 W and 5 W. The circuit topology consists of one high voltage transformer in a turn ratio of 1:5 up to 1:10, and one single semiconductor switch, operated in fly-back topology.

On the inside of the discharge vessel 34, a coating 52 is provided out of a luminescent material. The luminescent material is excited by primary light 50 emitted from the discharge and in turn emits secondary light 46 of different spectral composition depending on the choice of luminescent material.

In the currently preferred embodiment, the luminescent material is $YPO_4$:Bi. Other compositions, such as those mentioned in U.S. Pat. No. 6,398,970, which is incorporated herein by reference, may alternatively be used.

The upper end cover 14 shown in FIG. 3 further comprises a central control unit 56 to control operation of the lamp 32 and the ballast 48 to supply the control circuitry and the ballast 48 with electrical power. Connected to control unit 56 are a mechanical closure sensor 58, a UV photo sensor 60 arranged within a sensor holder 62, and a display 64 and a user control element 66 on the outside of upper end cover 14.

In accordance with the function of control element 56, the device 10 may be operated as follows:

In order to disinfect water, the container 12 may be opened by removing the top cover 14. Water may then by filled into the lower part 16 of the container housing 12.

Then, the disinfection process is activated by pressing the button 66 on the top cover 14. Before starting the lamp 32, the control unit 56 first checks the closure status of the container 12. If the mechanical closure sensor 58 indicates that the top cover 14 is firmly seated on the lower part 16, the UV treatment is started by powering up the ballast 48 to produce a suitable alternating voltage that is supplied to the electrodes 42, 44 of the lamp 32. Thus a discharge is ignited in the discharge space 40 emitting primary light 50 towards the luminescent layer 52. In turn, secondary light 46 is emitted into the interior volume 24 to treat the contained water.

The water contained in the interior volume 24 is then treated over a period of time by the UV light emitted from the lamp 32 through its lower wall 38 acting as a window. The UV treatment is effective to disinfect the water, on one hand directly by the UV radiation which damages the DNA of microorganisms in the water and on the other hand by oxidants created in the water and the remaining air by the UV radiation, such as ozone and peroxide. A reflectivity of the container wall helps to increase the average irradiance level within the water.

During treatment, the UV sensor 60 constantly measures the received intensity of UV light. As illustrated in FIG. 2, the UV sensor 60 is arranged on sensor holder 62 such that it receives light from the lamp 32 via reflection only, where the major part of the sensor signal is generated by the reflective bottom surface 26 of the container. The sensor holder 62 shields the sensor 60 from direct light 46 of the lamp 32. The intensity values delivered by sensor 60 are processed within the control unit 56 by calculating an integral value over time, corresponding to a UV dose value.

In this way, the control unit 56 ascertains that the water contained in the interior volume 24 is treated at least by a predetermined dose of UV light, thereby ensuring efficient disinfection.

After the predetermined minimum dose value has been reached, the control unit 56 signals via the display 64 the end of the treatment. The display 64 may also be used to signal any errors, e.g. if closure of the container 12 is not detected or if the intensity of the UV light received at the sensor 60 is not sufficient, which may be due to a malfunction of the lamp 32 or if the water to be treated is not clear enough such that the UV light from the light 32 does not penetrate sufficiently.

In the above described first, preferred embodiment, the side wall 16 and bottom 18 of the container housing 12 consist of a single piece of stainless steel of a wall thickness of e.g. 0.3-1 mm, which renders the container sufficiently stable. The stainless steel material also reflects UVC radiation to a certain degree, such that the bottom surface 26 is sufficiently reflective for the intensity measurement described above. It is, of course, possible to increase the reflectivity, e.g. by an aluminum layer, which will increase the reflectivity by a factor of approximately 3.

While presently a stainless steel container with thick walls is considered optimum, because it is inexpensive, stable and reflective, it is alternatively possible to provide the side wall 16 of the container housing 12 with different materials.

Figures 4A, 4B:
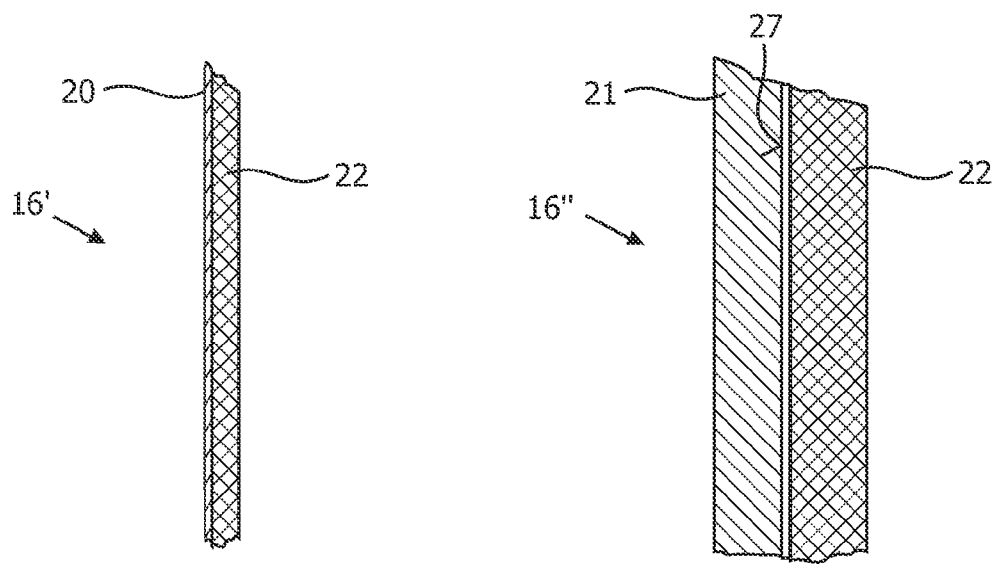
FIG. 4a, 4b show enlarged cross-sections of container walls according to alternative embodiments.

FIG. 4a shows a first alternative for a side wall 16' comprising a stainless steel wall 20 which is rather thin (below 0.3 mm) and is therefore covered for mechanical stability and shock absorption by a plastic cover 22. As in the preferred first embodiment, the stainless steel material may preferably be chosen as a food grade material.

FIG. 4b shows a further alternative, where a side wall 16" of a container housing 12 consists of a glass wall 21 with an (optional) reflective outside covering 27 of a thin aluminum layer, which may be provided e.g. by thermal evaporation. To protect both the glass wall 21 and the reflective layer 27, here also an outer plastic cover 22 is provided. In particular, a shock absorbing material like soft plastic rubber may be used to reduce a risk of breakage. Regular glass material may be used for the container wall 21, such that a relatively inexpensive container is obtained which is suitable to contain drinking water (food grade). However, regular glass material, e.g. with 70% silica, will absorb a large portion of UV radiation, thus reducing the intensity in the interior volume 24. It is thus preferred to use Quartz glass, i.e. glass made out of silica of high purity (e.g. more than 95% silica). Quartz glass is partly transparent for UVC radiation, such that the UV light will be reflected at the reflective layer 27.

FIGS. 5, 6 show a second embodiment of a disinfecting device 110. The alternative device 110 is intended to be used for the disinfection of objects rather than liquids. In the following, only the differences between this alternative embodiment and the first embodiment described above will be explained. Parts common between the embodiments will be designated by like reference numerals.

In the second embodiment of a disinfecting device 110, a top cover 14 is preferably fixed to the cylindrical container housing 16. Alternatively, the top cover 14 may also in the second embodiment be detachable as described above. The cylindrical housing 16 is open at the bottom and may be closed by a bottom cover 117.

As illustrated in FIG. 6, an object 125 may be placed within the interior volume 24, either as illustrated by placing it within the bottom cover 117, or, alternatively, by placing the object 125 on any flat surface and putting the container housing 16 over it.

Operation of the disinfection device 110 is effected as described above for the first embodiment. For a fixed lamp cover lid 14, a mechanical closing switch (not shown) may be arranged at the removable bottom cover 117; alternatively, or in addition, closure of the interior volume 24 is detected by the optical sensor 60 which measures also the intensity of visible light. The signal from the sensor 60 is evaluated in the control unit 56 to start the disinfecting process only if no ambient light is received at the sensor 60.

The safety function using the optical sensor 60 guarantees that the UV lamp is only allowed to switch on if the optical sensor 60 is free of irradiation in the visible range. The safety level can be increased by using the following embodiment: An additional light source, e.g. an LED, is provided at the device, without being in direct optical contact with the optical sensor 60. The LED emits light towards the opposite end cover, which is at least partly reflective for the light from the LED, preferably in the visible or near visible range between 380 and 800 nm. The optical sensor 60 is irradiated by the back reflected light of the LED if and only if the opposite cover is closed. A maximum safety is reached if two optical sensors are used: A first optical sensor which must be free of irradiation before the UV lamp is switched on; and a second optical sensor which must be irradiated to a predefined minimum level by the described LED signal before the UV lamp is switched on.

Figure 7:
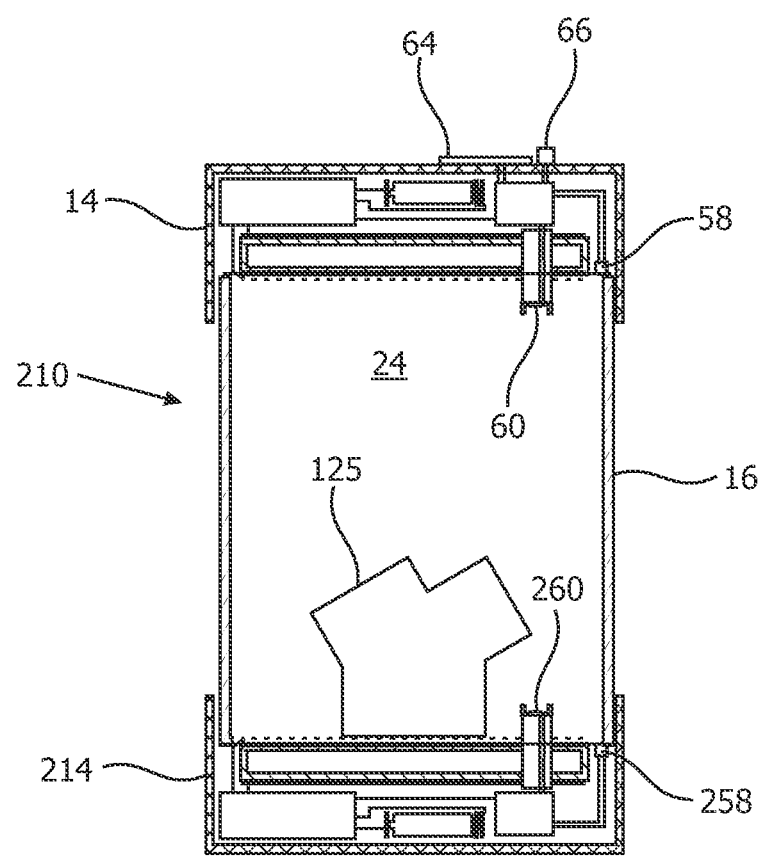
FIG. 7 shows a cross-sectional side view of a third embodiment of a disinfecting device.

FIG. 7 shows a third embodiment of a disinfecting device 210. The alternative device 210 differs from the above discussed embodiments in that it not only contains a detachable top cover 14 including a dielectric barrier discharge lamp and driver circuitry, but also a quasi identical detachable bottom cover 214 which also comprises a dielectric barrier discharge lamp and associated driver circuitry.

As in the above embodiments, side wall 16 of the container housing 12 is preferably of stainless steel (but other materials as discussed above may alternatively be chosen).

In the disinfecting device 210 according to the third embodiment, an object 125 placed within the inner volume 24 or a liquid contained in the inner volume 24 (in this case, the connection between the detachable lower lid 214 and the side wall 16 of the container housing 12 is sealed by gaskets to prevent leakage) is very efficiently disinfected by UV-C radiation both from above and below. This aids in disinfection of an object by reducing shading effects. In the case of a liquid with limited penetration depth of UV radiation, disinfection by radiation from both sides is more efficient. Further, redundancy is achieved, where in the case of failure of one of the lamps the device 210 may still be used.

As shown in FIG. 7, both the upper lid 14 and the lower lid 214 comprise a mechanical closure sensor 58, 258 and an optical sensor 60, 260. The device 210 is operated as explained above by pressing the switch 66 of the upper lid 14. Operation is only started if both mechanical closure sensors 58, 258 indicate that the lids 14, 214 are firmly seated on the hollow cylindrical side wall 16. An electrical connection between the lids 14, 214 (not shown in FIG. 7) serves to connect the control units and synchronize operation.

During operation, the optical sensor 60 monitors the UV intensity received from the lamp arranged in the opposite end cover 214, whereas the optical sensor 260 of the lower lid 214 receives the UV light from the lamp in the top cover 14. Thus, both lamps are monitored.

As explained above, the ultraviolet light 46 emitted by the lamp 32 not only directly disinfects the contents of the interior volume 24, but also generates radicals, such as ozone or peroxides in the air or water contained within the interior volume 24. The radicals generated within the interior volume 24 serve to provide highly effective disinfection of an object 125 or a liquid contained within the interior volume 24.

The invention has been illustrated and described in detail in the drawings and foregoing description. Such illustration and description are to be considered illustrative or exemplary and not restrictive; the invention is not limited to the disclosed embodiments.

For example, it is possible to operate the invention in an embodiment, where the shape of the housing is different from the exemplary shapes shown in the figures. Further, the optical closure sensor of the second disinfecting device 110 may also be used in connection with the first embodiment. Likewise, a mechanical closure sensor may be provided in the second embodiment.

Other variations to the disclosed embodiments can be understood and effected by those skilled in the art in practicing the claimed invention, from the study of the drawings, the description, and the appended claims. In the claims, the word "comprising" does not exclude other elements or steps, and the infinite article "a" or "an" does not exclude a plurality. A single unit may fulfill the function of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS 10 device
12 container housing
14 top cover
16, 16', 16" side wall
18 bottom
20 steel container
21 inner glass container
22 outer plastic covering
24 inner volume
26 bottom surface
27 reflective layer
30 plastic housing
32 discharge lamp
34 glass vessel
36 upper wall
38 lower wall
40 discharge space
42 first electrode
44 second electrode 46 secondary light
48 ballast
50 primary light
52 coating
54 battery
56 central control unit
58 mechanical closure sensor
60 UV photo sensor
62 sensor holder
64 display
66 user control element
110 second embodiment of disinfecting device
117 bottom cover
125 object
210 third embodiment of disinfecting device
214 bottom cover
258 closure sensor
260 photo sensor

The invention claimed is:

1. A disinfecting device comprising:
a container housing having at least one side wall defining an interior volume;
at least a first end cover for attachment to a first end of said container housing; and
a dielectric barrier discharge lamp for emitting ultraviolet light, said dielectric barrier discharge lamp comprising a lamp vessel containing a gas filling and electrodes that are electrically insulated from said gas filling, where a discharge in said gas filling is caused by an alternating voltage applied to said electrodes during operation,
said lamp vessel having a planar window from which the ultraviolet light is emitted during said discharge,
said lamp vessel being arranged in said first end cover such that the ultraviolet light emitted through said planar window illuminates the interior volume of the container housing and disinfects contents placed in said container housing.

2. The device according to claim 1 where: P1 said lamp vessel has the shape of a planar disc, said electrodes being arranged on opposite sides of said disc; and
said window comprises one of said sides of said disc.

3. The device according to claim 1, where
said container housing defining the interior volume has a cylindrical shape.

4. The device according to claim 1, said device comprising:
a battery; and
a ballast device electrically connected to said battery for supplying said alternating voltage.

5. The device according to claim 1 where;
said container housing is shaped such that said interior volume can be filled with a liquid; and
said first end cover is removable to open said container housing.

6. The device according to claim 1 where
said container housing comprises a second end cover for attachment to a second end of said container housing disposed opposite to said first end of said container housing.

7. The device according to claim 5, said device comprising:
a closure sensor for detecting opening of said container housing; and
a control unit for operation of said discharge lamp only if no opening of the container housing is detected by said closure sensor.

8. The device according to claim 7, where said closure sensor comprises
a light source and a photo sensor arranged such that light radiated from the light source illuminates the photo sensor
only when said container housing is closed, said light source then indirectly illuminating said photo sensor via reflection.

9. The device according to claim 1, said device comprising
a photo sensor for sensing an intensity of ultraviolet light within said interior volume.

10. The device according to claim 9 where:
said photo sensor is arranged at said first end cover;
said container housing comprises a second end disposed opposite to said first end;
said second end comprises a reflective surface for reflecting said ultraviolet light emitted from said discharge lamp; and
said photo sensor is adapted to sense an intensity of ultraviolet light reflected by said reflective surface.

11. The device according to claim 9 comprising a control unit for processing a signal from said photo sensor,
said control unit being adapted to determine from said signal a UV dose value.

12. The device according to claim 9 where
said discharge lamp comprises a luminescent layer for emitting secondary ultra-violet light when stimulated by primary ultraviolet light from said discharge.

13. The device according to claim 1 where
said container housing comprises a second end cover disposed at a second end opposite to said first end of said container housing, said second end cover including a second lamp that is arranged for illuminating said interior volume with ultraviolet light.

* * * * *